US008834901B2

(12) United States Patent
d'Alarcao et al.

(10) Patent No.: US 8,834,901 B2
(45) Date of Patent: Sep. 16, 2014

(54) ELECTROCHEMICALLY DEGRADABLE POLYMERS

(75) Inventors: Marc d'Alarcao, Malden, MA (US); Pericles Calias, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 1492 days.

(21) Appl. No.: 11/665,234

(22) PCT Filed: Oct. 14, 2005

(86) PCT No.: PCT/US2005/037248
§ 371 (c)(1),
(2), (4) Date: Apr. 1, 2008

(87) PCT Pub. No.: WO2006/044795
PCT Pub. Date: Apr. 27, 2006

(65) Prior Publication Data
US 2009/0024074 A1    Jan. 22, 2009

Related U.S. Application Data

(60) Provisional application No. 60/618,654, filed on Oct. 14, 2004.

(51) Int. Cl.
A61K 8/02     (2006.01)
C08F 8/50     (2006.01)
A61K 9/00     (2006.01)

(52) U.S. Cl.
CPC *C08F 8/50* (2013.01); *A61K 9/0009* (2013.01)
USPC ..... 424/400; 424/426; 514/772.7; 514/772.4; 604/20; 528/220; 526/312

(58) Field of Classification Search
USPC ............... 514/772.7, 772.4; 604/20; 424/426; 528/220; 526/312
See application file for complete search history.

(56) References Cited

U.S. PATENT DOCUMENTS

| | | | |
|---|---|---|---|
| 4,346,172 | A | 8/1982 | Swartz |
| 4,882,150 | A | 11/1989 | Kaufman |
| 4,994,023 | A | 2/1991 | Wellinghoff et al. |
| 5,900,405 | A | 5/1999 | Urry |
| 6,123,861 | A | 9/2000 | Santini, Jr. et al. |
| 6,132,752 | A | 10/2000 | Pickett et al. |
| 6,183,781 | B1 | 2/2001 | Burke |
| 6,328,996 | B1 | 12/2001 | Urry |
| 6,348,558 | B1 | 2/2002 | Harris et al. |
| 6,565,960 | B2 | 5/2003 | Koob et al. |
| 6,582,926 | B1 | 6/2003 | Chilkoti |
| 6,586,354 | B1 | 7/2003 | Topolkaraev et al. |
| 6,620,308 | B2 | 9/2003 | Gilbert |
| 6,730,772 | B2 | 5/2004 | Shastri |
| 2002/0119305 | A1 | 8/2002 | Mrksich et al. |
| 2003/0099682 | A1 | 5/2003 | Moussy et al. |
| 2003/0188427 | A1 | 10/2003 | Say et al. |

FOREIGN PATENT DOCUMENTS

EP    0 182 765    5/1986

OTHER PUBLICATIONS

Kusnezow, W. et al., "Solid Supports for Microarray Immunoassays", *J. Mol. Recognit.*, v. 16, pp. 165-176, 2003.
Langer, R. et al., "Designing Materials for Biology and Medicine", *Nature*, v. 428, pp. 487-492, 2004.
Yousaf, M. et al., "Using Electroactive Substrates to Pattern the Attachment of Two Different Cell Populations", *PNAS*, V. 98, pp. 5992-5996, 2001.
Hodneland, C. et al., "Biomolecular Surfaces That Release Ligands Under Electrochemical Control", *J. Am. Chem. Soc.*, v. 122, pp. 4235-4236, 2000.
Yousaf, M. et al., "Turning on Cell Migration With Electroactive Substrates", *Angew. Chem. Int. Ed.*, v. 40, pp. 1093-1096, 2001.
Yousaf, M. et al., "Diels-Alder Reaction for the Selective Immobilization of Protein to Electroactive Self-Assembled Monolayers", *J. Am. Chem. Soc.*, v. 121, pp. 4286-4287, 1999.
Carpino, L. et al., "Reductive Lactonization of Strategically Methylated Quinone Propionic Acid Esters and Amides", *J. Org. Chem.*, v. 54, pp. 3303-3310, 1989.
Brannon-Peppas, L., "Polymers in Controlled Drug Delivery", *Medical Plastics and Biomaterials Magazine*, 1997.
LaVan, D. et al., "Small-Scale Systems for In Vivo Drug Delivery", *Nature Biotechnology*, v. 21, pp. 1184-1191, 2003.
Nakabayashi, N. et al., J. Polyl Sci. Part A,, vol. 7, 1969, pp. 1275-1278.
Iwabuchi, S., et al., J. Poly. Sci. Part A, vol. 9, No. 11, (Nov. 1, 1971), pp. 3405-3409.
Zheng, A. et al., J. Or. Chem., vol. 64, 1999, pp. 156-161.
Kwon, IC et al., Nature, vol. 354, No. 6351, (Nov. 28, 1991), pp. 291-293.
Weerapreeyakul, N. et al., Med. Chem. Research, vol. 10, No. 3, (Jan. 1, 2000), pp. 149-163.
European Search Report relating to Application No. 05808966 dated Oct. 4, 2010.
Iwabuchi et al., *Journal of Polymer Science*, Polymer Chemistry Edition, v. 9, pp. 3405-3409, 1971.

(Continued)

*Primary Examiner* — Wu-Cheng Winston Shen
*Assistant Examiner* — Jean Cornet
(74) *Attorney, Agent, or Firm* — Foley & Lardner LLP; Michel Morency

(57) ABSTRACT

The present invention discloses polymeric materials that incorporate a modified quinone moiety, either to cross-link the polymer or as a monomeric unit of the polymer. These polymeric materials can be efficiently degraded through electrochemical reduction of the quinone leading to rapid hydrolysis of the pendant chemical groups and degradation of the polymer. Quinone-containing compositions and methods of producing electrochemically degradable polymers are disclosed. The methods and compositions of the present invention can be used in a wide variety of applications, including, but not limited to, drug delivery, tissue regeneration, biomedical implants, and electronic systems.

3 Claims, 4 Drawing Sheets

(56) References Cited

OTHER PUBLICATIONS

Wegner et al., "Electron-Transfer Polymers. XXXI. Preparation of Difunctional Benzoquinones and Related Derivatives and Polymers", *Journal of Organic Chemistry*, v. 32, pp. 3155-3159, 1967.

Zheng, Ailian, A Redox-Sensitive Resi Linker for the Solid Phase Syntheses of C-Terminal Modified Peptides, J. Org. Chem, 1999, vol. 64, 156-161.

Biomolecular Surfaces that Release Ligands under Electrochemical Control; Hodneland et al.; Journal of the American Chemical Society 2000, 122, 4235-4236.

Canadian Office Action dated Oct. 26, 2012 in application No. 2,583,746.

Chinese Third Office Action dated Nov. 5, 2012 for CN Application No. 200580043063.4.

Japanese Office Action dated Oct. 9, 2012 in JP Appl. No. 2007-536998.

Susumu Iwabuchi, et al. Preparation and Ring-Opening Polymerization of 2,5-Dimethylhydroquinone-bis-&-lacone, Journal of Polymer Science Part A-1, 1971, vol. 9, No. 11, 3405-3409.

US Office Action on U.S. Appl. No. 11/665,234 Dtd Nov. 21, 2011.

ELECTROCHEMICALLY DEGRADABLE POLYMERS

RELATED APPLICATIONS

This application is the U.S. National Stage of International Application Number PCT/US2005/037248, filed Oct. 14, 2005, which claims the benefit of priority to U.S. Provisional Patent Application No. 60/618,654, filed Oct. 14, 2004. The entire contents of the foregoing applications are hereby incorporated herein by reference.

TECHNICAL FIELD OF THE INVENTION

The technical field of this invention is degradable polymers and, in particular, polymers that can be degraded in a controlled manner.

BACKGROUND OF THE INVENTION

There is increased interest in the synthesis of new degradable polymers that can be attributed, at least in part, to the growing use of synthetic polymers in medical applications. Degradable polymers are presently used in matrices for delivery of bioactive substances, as scaffolding in tissue engineering, in suture materials, for fracture fixation, in dental applications, as sealants, as well as in other applications. Ideally, these synthetic polymers should be capable of degradation and the degradation products should be compatible with the human body.

Drug delivery systems can also benefit from the use of degradable polymers, especially when they are designed so that they are incapable of releasing their agent or agents until they are placed in an appropriate biological environment. Depending upon the polymer, the environmental change can involve pH, temperature, or ionic strength, and the system can shrink, swell, or decompose upon a change in any of these environmental factors. Biodegradable polymers, for example, degrade within the body as a result of natural biological processes, eliminating the need to remove a drug delivery system after release of the active agent has been completed.

Most biodegradable polymers are designed to degrade as a result of hydrolysis of the polymer chains into biologically acceptable, and progressively smaller, compounds. In some cases, such as systems that employ polylactides, polyglycolides, or their copolymers, the polymers will eventually break down to lactic acid and glycolic acid, enter the Kreb's cycle, and be further broken down into carbon dioxide and water and excreted through normal processes. In some degradable polymer systems, the release rate can be tailored for the application. For example, in systems that use polyanhydrides or polyorthoesters, the degradation occurs primarily at the surface of the polymer, resulting in a release rate that is proportional to the surface area of the drug delivery system.

However, these biodegradable polymers do not allow for controlled degradation of the polymer. For example, the biodegradability of polyester polymers depends on the ability of the ester linkage in the polymer backbone to hydrolyze or decompose in the presence of water. Such polymers often do not allow for predictable control over the rate of degradation once the polymer is placed inside an aqueous environment. Moreover, such polymer systems do not typically permit one to vary the release rate following administration or implantation.

Thus, there is a need in the art for new compositions and methods of synthesizing polymers that are capable of degrading in a controlled manner, e.g., in response to changes in the local environment or external stimuli.

SUMMARY OF THE INVENTION

The present invention discloses polymeric materials that incorporate a modified quinone moiety, either to cross-link the polymer or as a monomeric unit of the polymer. These polymeric materials can be efficiently degraded through electrochemical reduction of the quinone leading to rapid release of the pendant chemical groups and degradation of the polymer. Quinone-containing compositions and methods of producing electrochemically degradable polymers are disclosed. The methods and compositions of the present invention can be used in a wide variety of applications, including, but not limited to, drug delivery, tissue regeneration, biomedical implants, and electronic systems.

The invention is based, in part, upon the incorporation of a modified quinone polymer moiety, either to cross-link the polymer or as a monomer in the preparation of the polymer. The terms "moiety," "quinone moiety," and "polymer moiety," as used herein, are intended to encompass both polymer cross-linkers and monomeric components of polymers. Electrochemical reduction of the quinone within the polymer leads to rapid hydrolysis of the pendant chemical groups and thereby results in degradation of the polymer and alteration of its properties.

The invention makes use of modified quinone moieties that can be incorporated into a polymer such that the resultant polymeric materials can be controllably degraded via electrochemical reduction. The electrochemically degradable polymers can have the core structure shown below:

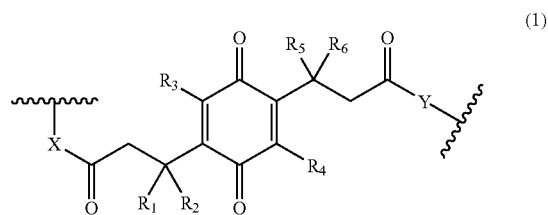

(1)

where $R_1$, $R_2$, $R_3$, $R_4$, $R_5$, and $R_6$ can be any organic functional groups including, but not limited to, hydrogen, alkyl, aryl, alcohol, ether, thiol, thioether, amine, cyano, halo, nitro, ketone, aldehyde, ester, amide, thioester, carbonate, carbamate, and urea. Any chemical moiety used as a reactive group in polymer cross-linking or as a reactive group in polymerization could be appended to the quinone structure at X and/or Y of structure (1). For example, the pendant groups X and Y can be any functional groups subject to degradation upon reduction of the quinone including, but not limited to, groups containing vinyl sulfone, epoxide, alkyl halide, alkene, amine, alcohol, acid halide, acid anhydride, sulfate, phosphate, isocyanate, isothiocyanate, and thiol. The pendant groups X and Y can be derived by substitution of any of the following elements: oxygen (O), sulfur (S), selenium (Se), nitrogen (N), phosphorous (P), and/or arsenic (As). The two groups X and Y can be identical or different. The resulting quinone could be used, as a cross-linker and/or a monomer, in the synthesis of electrochemically degradable polymers. The polymeric material of the present invention can be controllably degraded through electrochemical reduction. The degradation can be done by subjecting the polymer to an electric potential, a chemical reductant, or other agents that are capable of inducing chemical degradation. In one embodiment, the electrochemical reduction is induced by exposure to a change of electric potential between about 0.05 to about 1.0 V relative to Ag/AgCl reference electrode or between about 0.5 to about 1.0 V relative to Ag/AgCl reference electrode. Since the Ag/AgCl (silver/silver chloride) reference electrode is stable and easily prepared, it is often used as the reference electrode of choice. However, any technique for measuring electric potential can be used.

In addition, the degradation of the electrically-degradable polymers of the present invention can be modulated by varying the quinone cross-linker at $R_1$, $R_2$, $R_3$, $R_4$, $R_5$, and $R_6$. Varying $R_1$, $R_2$, $R_3$, $R_4$, $R_5$, and $R_6$, especially $R_3$ and $R_4$, affects the reduction potential of the quinone thereby affording an important means for controlling the rate, extent, and/or conditions of polymer degradation. For example, electron-donating groups such as methoxyl or dimethylamino in positions $R_3$ and/or $R_4$ can make the quinone less easily reduced and therefore can retard the degradation of the polymer. By contrast, electron-withdrawing groups, such as halogen or cyano in positions $R_3$ and/or $R_4$, can make the quinone more easily reduced and therefore can accelerate the degradation of the polymer.

In one embodiment, the invention provides an electrically-degradable polymer moiety comprising a quinone compound of the formula (1) wherein the polymer moiety is capable of degrading upon exposure to a change in electric potential. The quinone compound can be used to cross-link one or more monomers selected from the group comprising styrene, acrylates, methacrylates, 1,3-butadiene, isoprene, 2-vinylpyridine, ethylene oxide, acrylonitrile, methyl vinyl ketone, alpha-cyanoacrylate vinylidene cyanide, propyelene, butene, isobutylene, phosphorus acid, phosphonous acid, phosphinous acid, phosphoric acid, phosphonic acid, phosphinic acid, methylene bis (phosphonic acid), poly(vinylphosponic acid), aziridine, spermine, cadaverine, and putrecine.

The invention also provides a method of controlled release of pharmaceutical agents within a subject comprising implanting an electrically-controlled polymer derived from monomers and cross-linked using quinone cross-linkers having the core structure described above and electrically inducing chemical degradation of the polymer thereby releasing pharmaceutical agents.

In another aspect, the invention provides a drug delivery system comprising an electrically-degradable polymer comprising at least one quinone moiety, one or more pharmaceutical agents bound to the electrically-degradable polymer; and a current producing device electrically coupled to the polymer. In this system, the polymer is capable of undergoing electrochemical reduction resulting in the hydrolysis of the cross-linkers and controlled release of one or more pharmaceutical agents.

The electric current producing device can either provide a constant current or variable current, e.g., one which varies in response to changes in at least one internal parameter within the subject or in response to one or more external parameters. In another embodiment, the electrochemically-degradable polymers can be used in tissue regeneration as temporary scaffolds for the regeneration of various tissues. In addition, the electrochemically-degradable polymers can be used as temporary implants including vascular grafts, sutures, catheters, ligaments, bone fixation devices (bone plates, screws, and staples), and dental implants. Moreover, the electrically-degradable polymeric systems of the present invention permit switching from a first state to a second in response to a change in electric potential. Therefore, these systems can have application in microelectromechanical (MEM) devices, telecommunication devices and lithography.

DETAILED DESCRIPTION OF THE INVENTION

Figure 1:
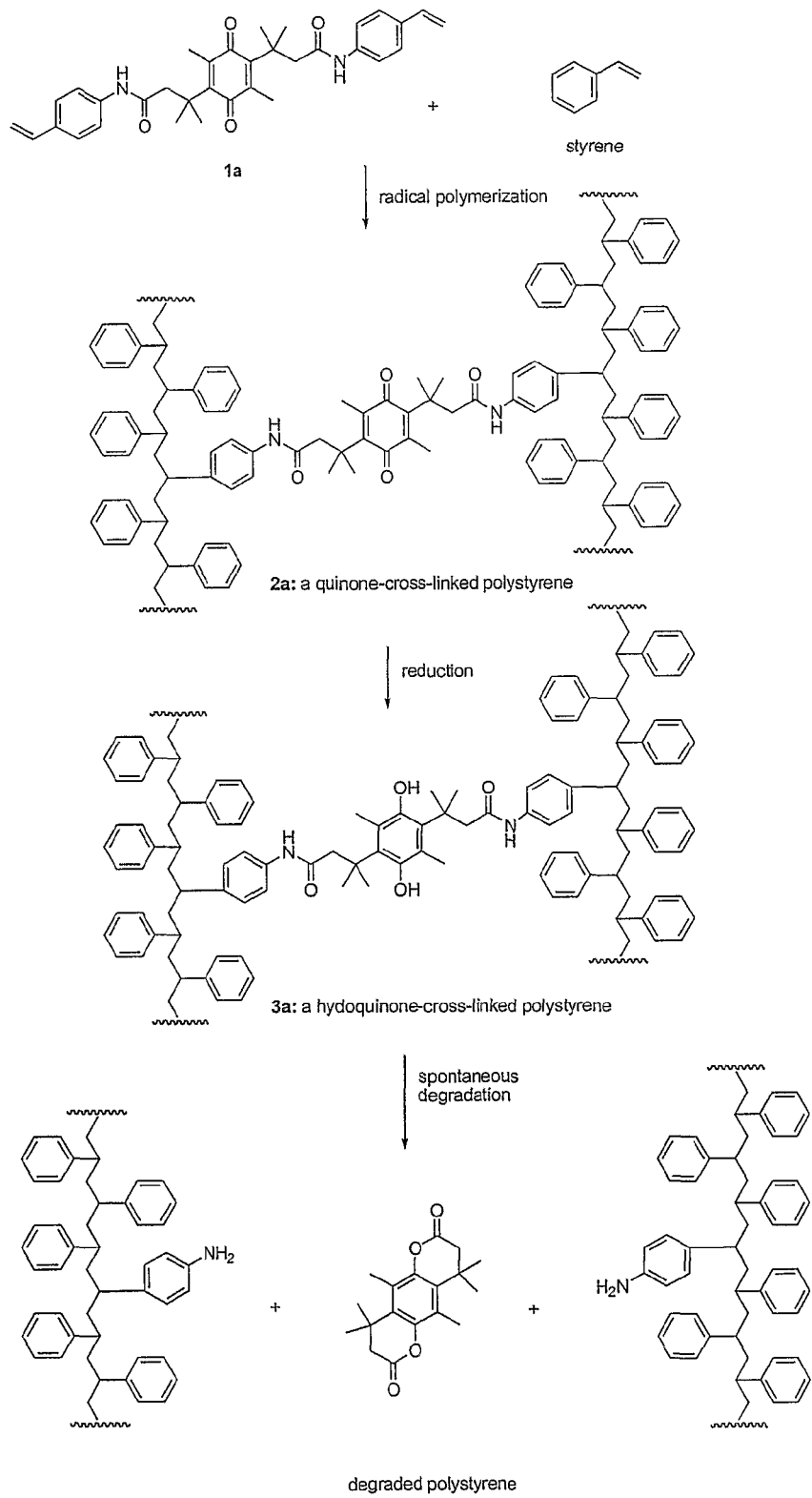
FIG. 1 is a schematic illustration of an electrochemically-degradable polymer of the present invention using styrene as the monomer.

The practice of the present invention employs, unless otherwise indicated, conventional methods of organic and polymeric chemistry within the skill of the art. Such techniques are explained fully in the literature.

The terminology used herein is for describing particular embodiments and is not intended to be limiting. Unless defined otherwise, all scientific and technical terms are to be understood as having the same meaning as commonly used in the art to which they pertain. For the purposes of the present invention, the following terms are defined below:

The term "alkyl" as used herein refers to an aliphatic hydrocarbon group, which may be straight or branched-chain, having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means 1 to about 4 carbon atoms in the chain, which may be straight or branched. The alkyl may be substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, 1-butyl, n-pentyl, 3-pentyl, methoxyethyl, carboxymethyl, methoxycarbonylethyl, benzyloxycarbonylmethyl, and pyridylmethyloxycarbonylmethyl.

The term "alkylene" as used herein refers to a straight or branched bivalent hydrocarbon chain of 1 to about 6 carbon atoms. The alkylene may be substituted with one or more "alkylene group substituents" which may be the same or different, and include halo, cycloalkyl, hydroxy, alkoxy, carbamoyl, carboxy, cyano, aryl, heteroaryl or oxo. Preferred alkylene groups are the lower alkylene groups having 1 to about 4 carbon atoms. Representative alkylene groups include methylene, ethylene, and the like.

The term "amino" used herein refers to a group of formula $Z^1Z^2N$— wherein $Z^1$ and $Z^2$ are independently hydrogen; acyl; or alkyl, or $Z^1$ and $Z^2$ taken together with the N through which $Z^1$ and $Z^2$ are linked to form a 4 to 7 membered aza-heterocyclyl. Representative amino groups include amino ($H_2N$—), methylamino, dimethylamino, diethylamino, and the like.

The term "aryl" used herein refers to an aromatic monocyclic or multicyclic ring system of 3 to about 14 carbon atoms, preferably of 6 to about 10 carbon atoms. The aryl may be substituted with one or more "ring system substituents"

which may be the same or different, and are as defined herein. Representative aryl groups include phenyl, naphthyl, furyl, thienyl, pyridyl, indolyl, quinolinyl or isoquinolinyl.

I. Polymeric Structures

The physical characteristics of the resulting polymer can be controlled by varying the type of substituted monomers that are cross-linked with the quinone cross-linker. The physical characteristics are important in determining the consistency of the polymer and what types of processing steps the polymer can withstand and, thus will determine which applications particular polymers will be most suited.

In one aspect of the invention, modified quinone moieties can be incorporated into a polymer such that the resultant polymeric materials can be controllably degraded via electrochemical reduction. The electrochemically degradable polymers can have the core structure shown below:

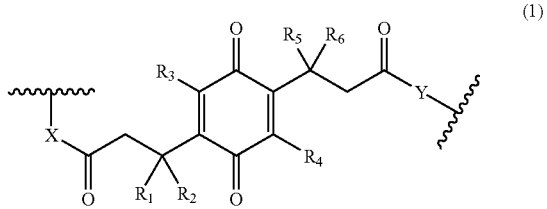

(1)

where $R_1$, $R_2$, $R_3$, $R_4$, $R_5$, and $R_6$ can be any organic functional groups including, but not limited to, hydrogen, alkyl, aryl, alcohol, ether, thiol, thioether, amine, cyano, halo, nitro, ketone, aldehyde, ester, amide, thioester, carbonate, carbamate, and urea. Any chemical moiety used as a reactive group in polymer cross-linking or as a reactive group in polymerization could be appended to the quinone structure at X and/or Y of structure 1. For example, the pendant groups X and Y can be any functional groups subject to degradation upon reduction of the quinone including, but not limited to, groups containing vinyl sulfone, epoxide, alkyl halide, alkene, amine, alcohol, acid halide, acid anhydride, sulfate, phosphate, isocyanate, isothiocyanate, and thiol. The pendant groups X and Y can be derived by substitution of any of the following elements: oxygen (O), sulfur (S), selenium (Se), nitrogen (N), phosphorous (P), and/or Arsenic (As). The two groups X and Y can be identical or different. The resulting quinone could be used, as a cross-linker and/or a monomer, in the synthesis of electrochemically degradable polymers.

Electrically-degradable polymers cross-linked with a modified quinone of the present invention can be made from polymerization, condensation, or other reaction of any combination of monomers selected from the group consisting of styrene, acrylates, methacrylates, 1,3-butadiene, isoprene, 2-vinylpyridine, ethylene oxide, acrylonitrile, methyl vinyl ketone, alpha-cyanoacrylate vinylidene cyanide, propyelene, butene, isobutylene, phosphorus acid, phosphonous acid, phosphinous acid, phosphoric acid, phosphonic acid, phosphinic acid, methylene bis(phosphonic acid), poly(vinylphosponic acid), aziridine, spermine, cadaverine, and putrecine.

In one embodiment, electrically-degradable polymers cross-linked with a modified quinone according to the methods of the present invention can include polymers consisting of modified carbohydrates including, but not limited to, derivatives of cellulose, sucrose, chitosan, alginate, hyaluronic acid, guar gum, and gelatin.

In yet another embodiment, electrically-degradable polymers cross-linked with a modified quinone according to the methods of the present invention can include polymers formed from the polymerization, condensation or modification of amino acids including, but not limited to, lysine, arginine, phenol, tyrosine, and cysteine or modified versions thereof.

The resulting polymers of the present invention comprise one or more linkages selected from the group consisting of ester, ether, amine, amide, urethane, ketone, anhydride, carbonate, phosphodiester, silicone, disulfide, urea, and phenolic.

The choice of linkage is based upon the desired use of the resultant polymer. For example, the presence of an ester linkage provides the necessary functionality to permit degradability, particularly biodegradability, since the ester linkage undergoes hydrolysis under mildly basic conditions, such as those found in vivo. Other linkages, such as amides, require severe conditions in order to decompose. The amide linkage requires more stringent conditions and is not easily hydrolyzed even under strongly acidic or basic conditions. Therefore, in vivo, the only available route for cleavage of an amide bond is enzymatic, and that cleavage is often specific to the amino acid sequence. The highly crystalline nature of polyamides, e.g., nylon, further slows degradation by preventing or blocking access to the amide bond by water molecules and enzymes.

II. Examples of Quinone Structures

In one embodiment of the present invention, styrene can be used as the monomer. An exemplary modified quinone cross-linker is depicted as 1a ($R_1=R_2=R_3=R_4=R_5=R_6=CH_3$, X=Y=p-vinylaniline) shown in FIG. 1. In this example, quinone 1a is used as a cross-linking agent in the synthesis of a polystyrene-based polymer in place of the common cross-linking agent, divinylbenzene. The product, polystyrene polymer 2a, comprises the quinone moiety in the cross-links between strands. Upon reduction, which can be either electrically, chemically, or by some other method, hydroquinone-cross-linked polymer 3a is formed. Polymer 3a can spontaneously undergo cleavage of the amide linkages in the cross-links, leading to degraded polystyrene without cross-links and thereby changing the material properties of the polymer substantially.

Figure 2:
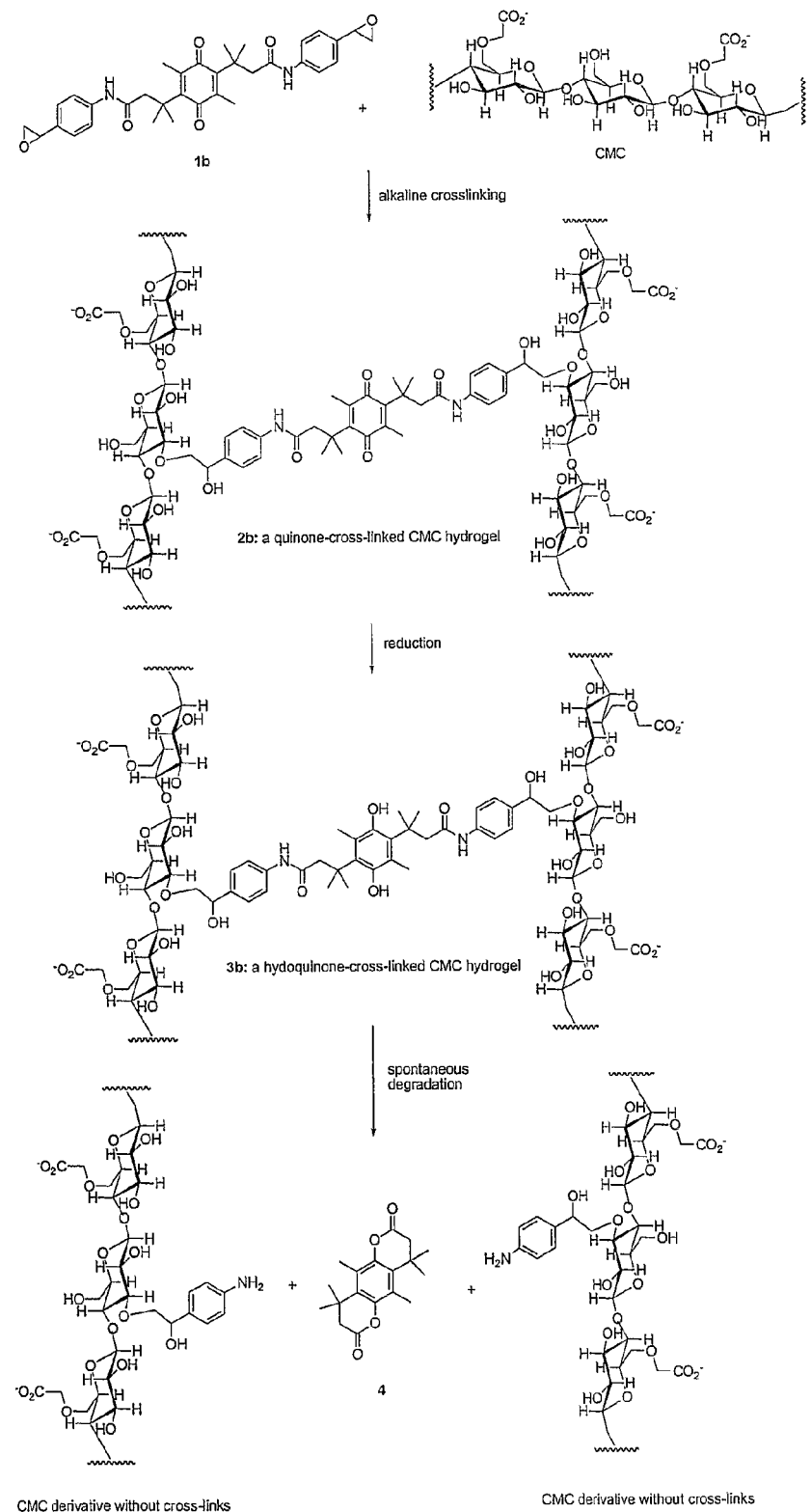
FIG. 2 is a schematic illustration of an electrochemically-degradable polymer of the present invention using carboxymethylcellulose (CMC) as the cross-linked polymer.

In another embodiment of the present invention, carboxymethylcellulose (CMC) can be crosslinked with a modified quinone of the present invention. An example of an exemplary modified quinone structure, 1b, ($R_1=R_2=R_3=R_4=R_5=R_6=CH_3$, X=Y=p-oxiridinoaniline) is shown in FIG. 2. In this example, the modified quinone 1b is used as a cross-linking agent for carboxymethylcellulose (CMC) in place of the common cross-linking agent, epichlorohydrin. The product is CMC hydrogel 2b that contains the quinone moiety in the cross-links between strands. Upon reduction, either electrically, chemically, or by some other method, hydroquinone-crosslinked hydrogel 3b is formed. Polymer 3b can spontaneously undergo cleavage of the amide linkages in the cross-links, thus leading to a CMC derivative without cross-links and thereby changing the material properties of the hydrogel substantially.

Figure 3:
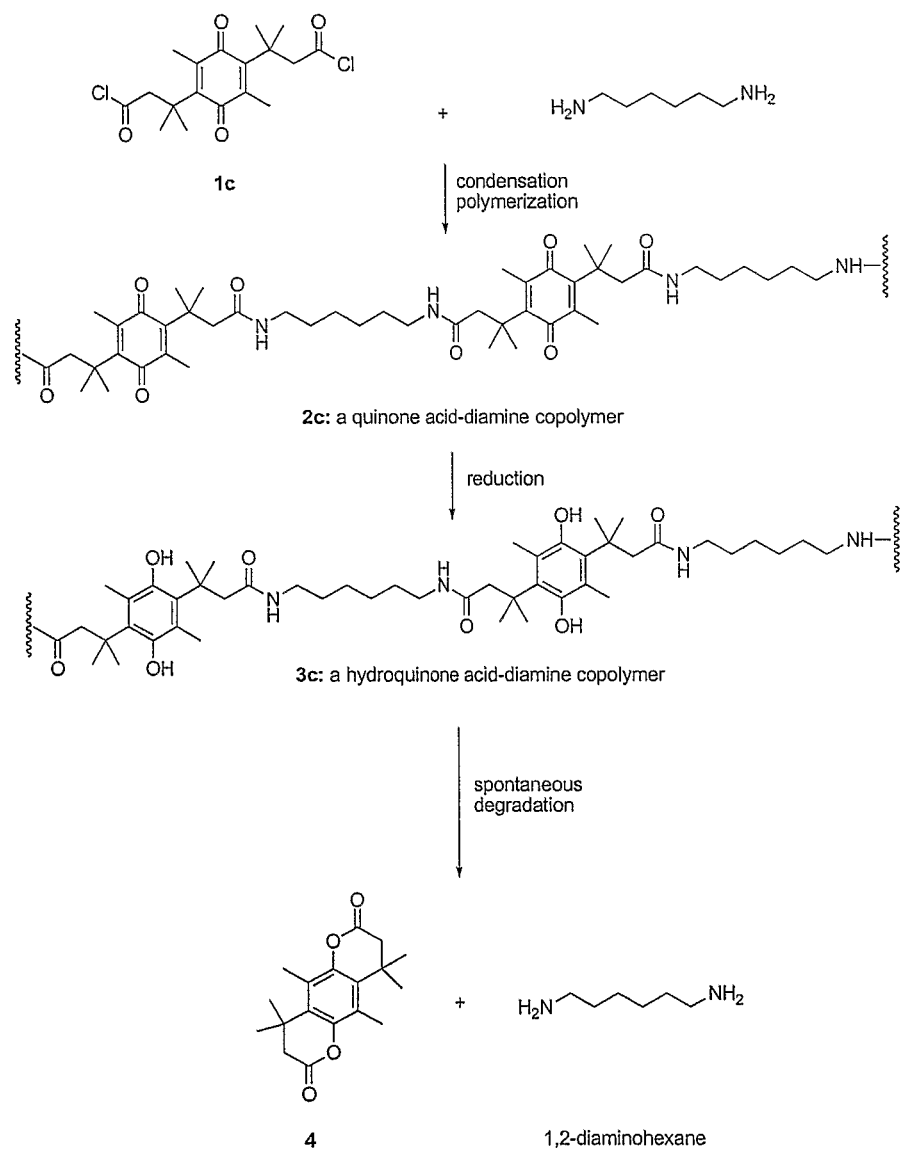
FIG. 3 is a schematic illustration of an electrochemically-degradable copolymer of the present invention using 1,2-diaminohexane and quinone monomers.

In yet another embodiment of the present invention, a copolymer can be formed using a quinone and 1,6-diaminohexane as monomers. An example of a quinone useful for this embodiment is depicted as the quinone structure is 1c ($R_1=R_2=R_3=R_4=R_5=R_6=CH_3$, X=Y=Cl) shown in FIG. 3. In this example, quinone 1c is used as one of the monomers in a condensation polymer with 1,6-diaminohexane. The product, the condensation quinone acide-diamine copolymer 2c, contains the quinone moiety in alternating units with the diaminohexane. Upon reduction, hydroquinone-containing polymer 3c can be formed. Polymer 3c can spontaneously undergo cleavage of the amide linkages holding the polymer together, leading to completely degraded polymer.

Any chemical moiety used as a reactive group in polymer cross-linking or as a reactive group in polymerization could be appended to the quinone core structure 1 at X and/or Y. The resulting quinone can be used in the electrochemically degradable synthesis of polymers. The choice of modified quinone crosslinker and monomers depends on the desired use of the resultant polymer.

In some embodiments, the electrochemically-degradable polymers of the present invention can be applied to or blended with another biocompatible polymeric material, including biodegradable or non-biodegradable polymeric materials. Combining the electrochemically-degradable polymers with other polymeric material allows for further control of the degradation rate.

III. Uses for Electrically Degradable Polymers

The methods and constructs of the present invention can be used in drug delivery, tissue regeneration, biomedical implants, electronic systems, microchip design, and/or chemical/biological warfare.

The size and shape of the electrochemically degradable polymers can be selected based upon the desired use. For example, the polymers can be formulated into pellets, films, microspheres, polymerizing gels, hydrogels, wafers, coatings, etc. In some embodiments, the electrochemically degradable polymers of the present invention can be formulated into microparticles, which can be used, for example, in oral delivery systems and in subcutaneously injected delivery systems. For example, microparticles of poly(lactide-co-glycolide) (PLGA) can be prepared in a fairly uniform manner to provide essentially nonporous microspheres. Upon electrochemical stimulation, the polymers can be induced to degrade resulting in polymer fragments. In some embodiments, the polymer fragments can be adsorbed by the body.

Drug Delivery

Methods for sustained or controlled drug release can utilize a drug dispersed in an electrically degradable polymer matrix, which can be implanted, administered orally or injected. Exemplary polymers to be used in such applications include poly(lactic acid) and poly(lactic acid-co-glycolic acid) crosslinked with a modified quinone of the present invention. These polymers undergo slow hydrolysis in vivo, releasing the entrapped drug. The polymer degradation products are the parent acids, which are absorbed by the body.

Polymer/drug matrix particles to be administered via injection must have a size range typically on the order of 200 microns or less. The size and morphology of polymer/drug matrix particles depends upon the fabrication method employed, and the formation of small polymer/drug matrix particles in which the drug is a protein is currently limited to a few techniques. For example, polymer/protein matrix particles comprising poly(lactic acid) and either trypsin or insulin, can be prepared by both an oil/water emulsion method and a neat mixing method at elevated temperature (Tabata et al., *J. Cont. Release* 23: 55-64 (1993)). The polymer/protein matrices thus formed can be subsequently ground into granules.

In another embodiment, the electrochemically degradable polymers can be used in drug delivery system comprising an electrically degradable polymer and a current producing or electric charge generating device. The electrically degradable polymer can, for example, be used to house one or more pharmaceutical agents. Alternatively, the electrochemically degradable polymer could be used as a covering to drug reservoirs in implantable devices. The current producing device can be electrically coupled to the degradable polymer, such that the polymer is capable of undergoing electrochemical reduction resulting in the hydrolysis of the quinone crosslinkers and controlled release of one or more pharmaceutical agents.

The electric current producing device can either provide a constant current or variable current, e.g., one which varies in response to changes in at least one internal parameter within the subject or in response to one or more external parameters.

Non-limiting examples of the internal parameter include diagnostic markers (such as cancer markers including carcinoembryonic antigen (CEA), prostate-specific antigen (PSA), alpha-fetoprotein (AFP), beta-human chorionic gonadotropin (β-HCG), carbohydrate antigen 125 (CA-125), carbohydrate antigen 15-3 (CA 15-3), carbohydrate antigen 19-9 (CA 19-9), Beta$_2$ ($β_2$)-microglobulin, lactate dehydrogenase), cholesterol, blood pressure, temperature, energy expenditure, activity level, heart rate, blood acidity, blood alcohol, ammonia, ascorbic acid, bicarbonate, bilirubin, blood volume, calcium, carbon dioxide pressure, carbon monoxide, CD4 cell count, ceruloplasmin, chloride, complete blood cell count (CBC), copper, creatine, kinase (CK or CPK), creatine kinase isoenzymes, creatinine, cytokines, electrolytes (calcium, chloride, magnesium, potassium, sodium), erythrocyte sedimentation rate (ESR or Sed-Rate), glucose, hematocrit, hemoglobin, iron, iron-binding capacity, lactate (lactic acid), lactic dehydrogenase, lead, lipase, zinc, lipids, cholesterol, triglycerides, liver function tests (i.e., bilirubin (total), phosphatase (alkaline), protein (total and albumin), transaminases (alanine and aspartate), prothrombin (PTT)), magnesium mean corpuscular hemoglobin (MCH), mean corpuscular hemoglobin concentration (MCHC), mean corpuscular volume (MCV), osmolality, oxygen pressure, oxygen saturation (arterial), phosphatase, phosphatase, phosphorus, platelet count, potassium, prostate-specific antigen (PSA), total blood proteins, albumin, globulin, prothrombin (PTT), pyruvic acid, red blood cell count (RBC), sodium, thyroid-stimulating hormone (TSH), transaminase, alanine (ALT), aspartate (AST), urea nitrogen (BUN), BUN/creatinine ratio, uric acid, vitamin A, white blood cell count (WBC), etc. Changes in one or more internal parameter can be continuously monitored. An automatic turn-on protocol can be triggered once the change in one or more internal parameter reaches a preset limit. The current producing device can also be capable of being controlled externally, by, for example, the subject and/or doctor. For example, the drug delivery system can be used as an on-demand delivery of analgesics wherein NSAIDS or other pain medication can be controllably released when the subject activates the current producing device upon sensing pain.

Non-limiting examples of the external parameter that can be monitored by the current producing device include biochemical/biological agents (i.e., aerosolized or lyophilized agents like *Bacillus anthracis, Yersia pestis, Francisella tularensis*, brucellosis, tularemia, and Venezuelan Equine Encephalitis ("VEE"), *Bacillus globigii, Clostridium perfringens, Clostridium botulinum*, ricin, SEB (Staphococcal Enterotoxin B)), chemical agents such as cyanide gas and mustard gas and those including organo-phosphate compounds such as those known as GA, GB, GD, GF, and VX, viruses responsible for diseases such as smallpox, chicken pox, german measles, herpes, hepatitis, AIDS, rabies, polio, and influenza (See, for example, U.S. Pat. No. 6,777,228 and U.S. Pat. No. 6,472,155 for systems for monitoring biological agents, which are hereby incorporated by reference). For example, the drug delivery system can be used as an on-demand delivery of antidotes for biochemical/biological warfare wherein antidotes (i.e., penicillin for bubonic plague) could be controllably released when the external parameter exceeds a predetermined threshold.

The electrically degradable polymer can be used either inside or outside the body in proximity to the area to be treated. The system has applications in transdermal, subcutaneous and intravenous use. For example, this system can be used as a transdermal drug delivery system for transdermal delivery of medical or veterinary pharmaceutical agents.

In some embodiments, the electrically degradable polymer can be use in a drug delivery system having uses in treatment or monitoring of conditions such as, for example, pain, arrhythmia, cancer, diabetes, angiogenesis, restenosis, edema, infection, infectious diseases, sepsis, post operative adhesions, cell signaling, immunologic responses, tissue/implant rejection, neurodegenerative diseases, and hormone imbalances.

Tissue Engineering

In another embodiment, the electrochemically-degradable polymers can be used in tissue regeneration as a temporary scaffold for the regeneration of various tissues including, but not limited to, cartilage, epithelium, cardiac, skeletal, vascular, and may also be used as a temporary nerve guide. The electronically-degradable polymers can be used to seed any combination of cell types including, but not limited to, endothelial cells, parenchymal cells such as hepatocytes, stem cells, Islet cells, and other organ cells, muscle cells, cells forming bone and cartilage such as osteoblasts and chondrocytes and nerve cells, from mammalian tissue or lower animals and genetically-engineered cells. A combination of polymers can be formed prior to cell growth and attachment prior to in vivo or ex vivo use. The electrochemically-degradable polymers can blended with another polymeric material, applied as a coating on the surface of another material, or be used to form the material itself.

Porous polymer scaffolds comprising electrically degradable polymers can be shaped into articles for tissue engineering and tissue guided regeneration and repair applications, including reconstructive surgery. Scaffold applications include the regeneration of tissues such as nervous, musculoskeletal, cartilaginous, tendenous, hepatic, pancreatic, ocular, integumentary, arteriovenous, urinary or any other tissue forming solid or hollow organs. Scaffolds can be used as materials for vascular grafts, ligament reconstruction, adhesion prevention and organ regeneration. In one embodiment, the polymer scaffold provides physical support and an adhesive substrate for isolated cells during in vitro culturing and subsequent in vivo implantation in the human body. An alternate use of electrically degradable polymer scaffolds is to implant the scaffold directly into the body without prior culturing of cells onto the scaffold in vivo. Once implanted, cells from the surrounding living tissue attach to the scaffold and migrate into it, forming functional tissue within the interior of the scaffold. Regardless of whether the scaffold is populated with cells before or after implantation, the scaffold is designed so that as the need for physical support of the cells and tissue diminishes over time, the scaffold can degrade upon electrical stimulation. The controllable degradation of the electrically degradable scaffold can be catalyzed via reduction of the modified quinone cross-linkers of the polymer scaffold. For example, once the doctor determines that engineered tissue has regenerated, a voltage can be supplied, either inside or outside the body, causing degradation of the scaffold.

Materials which can be used for tissue engineering (implantable matrices) include sutures, tubes, sheets, adhesion prevention devices (typically films, polymeric coatings applied as liquids which are polymerized in situ, or other physical barriers), and wound healing products (which vary according to the wound to be healed from films and coating to support structures). Both normal and genetically engineered nerve cells optionally can be seeded on the implants, to help replace lost function.

As described by Langer et al., *J. Ped. Surg.* 23 (1), 3-9 (1988), WO88/03785 and EPA 88900726.6 by Massachusetts Institute of Technology, a matrix for implantation to form new tissue should be a pliable, non-toxic, porous template for vascular ingrowth. The pores should allow vascular ingrowth and the seeding of cells without damage to the cells or patient. These are generally interconnected pores in the range of between approximately 100 and 300 microns. The matrix should be shaped to maximize surface area, to allow adequate diffusion of nutrients and growth factors to the cells. In the preferred embodiment, the matrix is cross-linked with a modified quinone and formed of an electrically-degradable bioabsorbable, or biodegradable, synthetic polymer such as a polyanhydride, polyorthoester, or polyhydroxy acid such as polylactic acid, polyglycolic acid, and copolymers or blends thereof. Non-degradable materials can also be used to form the matrix. Examples of suitable materials include ethylene vinyl acetate, derivatives of polyvinyl alcohol, teflon, nylon, polymethacrylate and silicon polymers. The preferred non-degradable materials are ethylene vinyl acetate meshes and polyvinyl alcohol sponges. Commercially available materials may be used. Polymers for use in the matrix can be characterized for polymer molecular weight by gel permeation chromatography (GPC), glass transition temperature by differential scanning calorimetry (DSC), thermal stability by thermal gravimetric analysis (TGA), bond structure by infrared (IR) spectroscopy, toxicology by initial screening tests involving Ames assays and in vitro teratogenicity assays, and by implantation studies in animals for immunogenicity, inflammation, release and degradation studies.

The electrically-degradable polymers may be implanted in vivo into a patient in need of therapy to repair or replace damaged cells or tissue, such as nervous system tissue. Scaffolds for tissue engineering can be coated with, or made of, electrically-degradable polymers to enhance regeneration, growth or function of implanted cells or cells which migrate into, attach and proliferate within the implanted matrices. Materials which can be used for implantation include sutures, tubes, sheets, adhesion prevention devices (typically films, polymeric coatings applied as liquids which are polymerized in situ, or other physical barriers), and wound healing products (which vary according to the wound to be healed from films and coating to support structures). To enhance the effectiveness of the treatment, compositions which further promote nervous tissue healing, such as proteins, antibodies, nerve growth factors, hormones, and attachment molecules, can be applied together with the polymer, and optionally can be covalently attached to the polymer or a polymeric support material. Those skilled in the art can readily determine exactly how to use these materials and the conditions required without undue experimentation.

Molecules such as attachment molecules or bioactive molecules such as growth factors can be provided on the electrically-degradable polymers, and may be optionally covalently or non-covalently attached to the polymers. Attachment molecules are defined as any natural or synthetic molecule which is specifically bound by cell surface receptors. These include natural and synthetic molecules having one or more binding sites. Examples of natural molecules are extracellular matrix factors such as fibronectin and laminin. Examples of synthetic molecules are peptides containing the binding sites of fibronectin. In some embodiments, attachment of the cells to the polymer is enhanced by coating the polymers with compounds such as basement membrane components, gelatin, gum arabic, collagens types I, II, III, IV, and V, fibronectin, laminin, glycosaminoglycans, mixtures thereof, and other materials known to those skilled in the art of cell culture. Extracellular matrix molecules (ECM) include compounds such as laminin, fibronectin, thrombospondin, entactin, proteoglycans, glycosaminoglycans and collagen types I through XII. Other natural attachment molecules include simple carbohydrates, complex carbohydrates, asialoglycoproteins, lectins, growth factors, low density lipoproteins, heparin, poly-lysine, thrombin, vitronectin, and fibrinogen. Synthetic molecules include peptides made using conventional methods to incorporate one or more binding sites such as R G D from fibronectin, L I G R K K T from fibronectin and Y I G S R from laminin.

Methods for attaching biological molecules to polymeric substrates available in the art may be used. Methods for applying attachment molecules to substrates include: attachment of molecules to substrate by applying attachment molecules in a solution such as PBS or a high pH, carbonate buffer and adsorption of the molecules to the substrate surface; ionic binding of attachment molecules to substrate; covalent binding of molecules to the substrate surface by chemical reactions using reagents such as glutaraldehyde or carbodiimide; and drying of attachment molecules on the substrate surface.

Biomedical Implants

In another embodiment, the electrochemically-degradable polymers of the present invention can be used in biomedical implants. For example, the electrochemically-degradable polymers can be used as temporary implants including vascular grafts, sutures, catheters, ligaments, bone fixation devices (i.e., bone plates, screws, and staples), and dental implants.

Additional biomedical applications for electrically degradable polymers include use with fracture fixation, for example, as absorbable orthopedic fixation devices. In particular, such electrically degradable polymers permit treatment of bone fractures through fixation, providing good tissue/material compatibility, and facile molding (into potentially complex shapes) for easy placement. Controlled degradation of the electrically degradable polymers permits optimum bone function upon healing. The materials can reestablish the mechanical integrity of the bone and subsequently degrade to allow new bone formation to bear load and remodel. These electrically degradable polymers maintain mechanical integrity while undergoing a gradual degradation and loss in size permitting bone ingrowth. In contrast to the traditional use of steel fixation devices, the electrically degradable polymer-based device is advantageous in those situations where the device is not needed permanently or would require removal at a later point in time. Also, metallic orthopedic devices shield stress during healing and can lead to bone atrophy.

Non-limiting examples of other polymeric materials that can be blended or coated with the electrically-degradable polymers include biocompatible materials which are not biodegradable, such as poly(styrene), poly(esters), polyurethanes, polyureas, poly(ethylene vinyl acetate), poly(propylene), poly(methacrylate), poly(ethylene), poly(ethylene oxide), glass, polysilicates, poly(carbonates), teflon, fluorocarbons, nylon, and silicon rubber. Other useful materials include biocompatible, biodegradable materials such as poly (anhydrides), poly(hydroxy acids) such as poly(glycolic acid) and poly(lactic acid), poly(lactide-co-glycolide), poly (orthoesters), poly(propylfumerate), proteins and polymerized proteins such as collagen, and polysaccharides and polymerized polysaccharides, such as glycosaminoglycans, heparin and combinations thereof.

Electronic Systems

The electrically-degradable polymeric systems of the present invention permit reasonably rapid switching from a first state to a second in response to a change in electric potential. By way of examples, these systems can have application in microelectromechanical (MEM) devices, telecommunication devices and lithography. For example, it can be employed as switches in photonic applications, such as a crossbar switch router for a fiber optic communications network, as actuable valves in microfluidicic systems, MEMs, and other electronic systems, such as to switch optical data packets. In addition, the electrically-degradable polymers can be used as a masking element in microchip design.

The electrically-degradable polymers can be used to provide an integral switching mechanism within a high density interconnect (HDI) circuit environment. Previous MEM based switches and actuators required the insertion of individual MEM parts into the HDI circuit and the subsequent routing of signals to the MEM structure, particularly when a large number of switches were required or high isolation of the switched signals was desired. The use of an integral MEM switch within an HDI structure will allow switches to be positioned in desired locations with a minimum of signal diversion and routing. In addition, it will not be necessary to handle and insert the fragile MEM actuators into cavities in the HDI circuit and suffer the yield loss of this insertion process. The use electrically-degradable polymers to fabricate integral switching mechanisms within HDI architecture will ultimately result in a lower cost system.

In one embodiment, a MEM based switch structure or actuator can be fabricated using traditional HDI processing steps. The switch structure can be operated by selectively passing current through the electrically-degradable polymer layers thereby causing them to heat above the transition temperature and causing a deformation of the heated layer.

In addition, polymers of the present invention can be designed such that they can be environmentally friendly. The creation of polymers in today's society and the exponential use in all areas of society has also created environmental concerns over whether such polymers will be able to degrade over time or will end up in landfills forever. Electrically-degradable polymers can be used to reduce the stress on the environment caused be the increasing use of polymeric materials.

EXAMPLES

The following examples illustrate practice of the invention. These examples are for illustrative purposes only and are not intended in any way to limit the scope of the invention claimed.

The present invention relates to polymeric materials capable of being degraded when exposed to an electric current. In particular, electrochemical reduction of the modified quinone moiety, which can be used to cross-link the polymer, can cleave the polymer resulting in efficient degradation. The following examples illustrate the synthesis of one exemplary polymer, polystyrene, using the methods of the present invention.

The general synthesis described in the examples comprise the three reaction steps illustrated below.

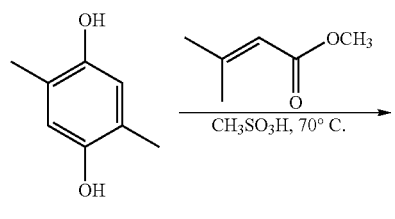

2,5-Dimethyl Hydroquinone

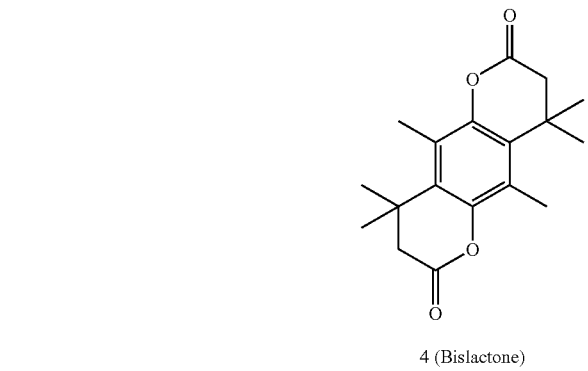

4 (Bislactone)

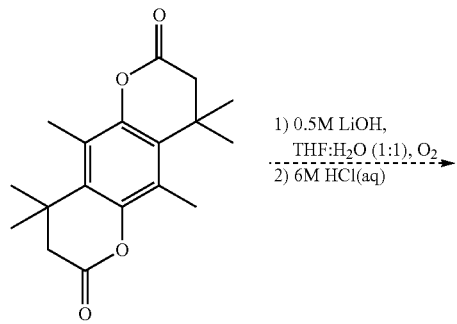

4

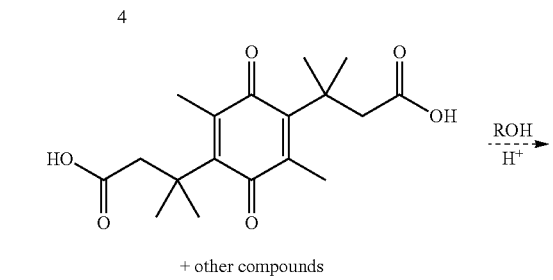

+ other compounds

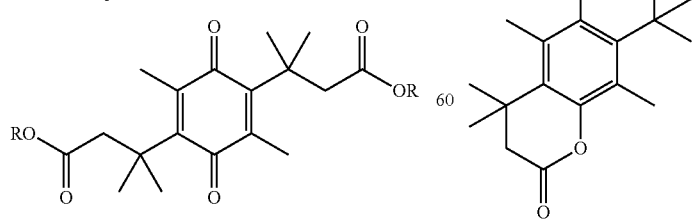

Example 1

Synthesis of Bislactone 4

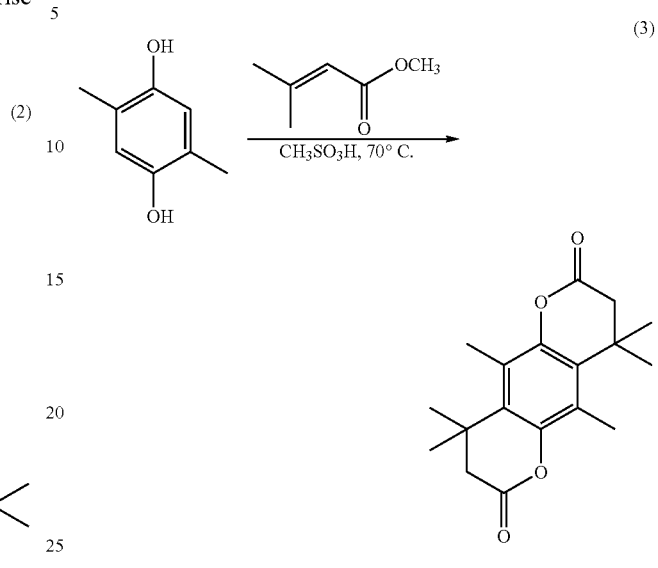

This example demonstrates an exemplary method of synthesizing bislactone 4. Methane sulfonic acid (1 mL) can be heated to 70° C. in an oil bath with stirring. To this, p-xylohydroquinone (91 mg, 0.658 mmol) and methyl β,β-dimethylacrylate (195 μL, 179 mg, 1.49 mmol) can be added and the reaction is allowed to proceed for 15 h at 70° C. After cooling to 20° C., the reaction mixture can be diluted with ice water (15 mL) and extracted with 4×20 mL of ethyl ether. The organic phase can then be washed with 2×50 mL of sat $NaHCO_3$, dried with $MgSO_4$, and the solvent can be removed in vacuo. A light orange solid (198 mg) will result. Purification by flash column chromatography ($CH_2Cl_2$) will yield 58.4 mg (0.180 mmol, 27%) of the lactone as a white solid. $R_F$ 0.44 ($CH_2Cl_2$); mp 280-282° C.; $^1$H NMR ($CDCl_3$) δ 2.59 (s, 4H, $CH_2$), 2.42 (s, 6H, $CH_3$), 1.48 (s, 12H, $CH_3$). (Anal. Calcd for $C_{18}H_{22}O_4$: C, 71.50; H, 7.33. Found: C, 71.22; H, 7.33.)

Example 2

Synthesis of Quinone Acid
($R_1$=$R_2$=$R_3$=$R_4$=$R_5$=$R_6$=$CH_3$, X=Y=OH)

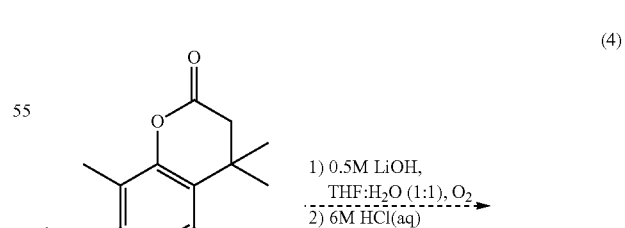

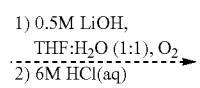

4

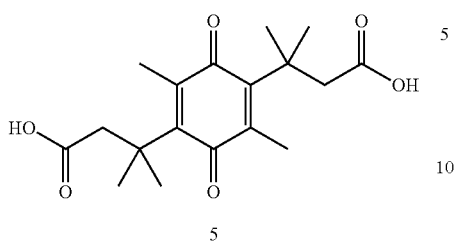

Figure 4:
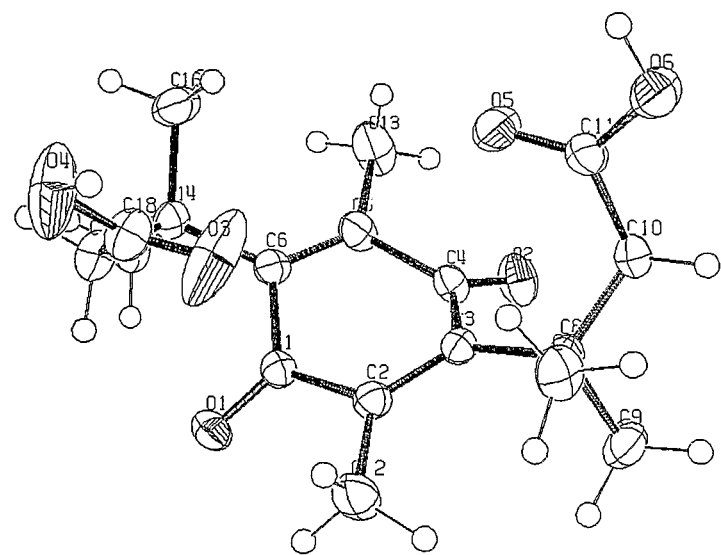
FIG. 4 is a three dimensional structure of the quinone acid 5.

This example demonstrates an exemplary method of synthesizing quinone acid ($R_1=R_2=R_3=R_4=R_5=R_6=CH_3$, $X=Y=OH$). The lactone 4 (150 mg) was dissolved in 15 mL of THF and 1M aqueous LiOH (15 mL) was added. The resulting turbid solution was stirred vigorously in an uncapped vessel at 20° C. for 4 h, after which TLC (silica, 5% EtOH/$CH_2Cl_2$) indicated complete reaction. The reaction mixture adjusted to pH 3 by addition of 6M aqueous HCl, and the mixture was extracted with EtOAc (3×50 mL). The extracts were washed with $H_2O$ (50 mL), brine (50 mL), dried ($MgSO_4$) and the solvent was evaporated to produce 159 mg (95%) of essentially pure quinone acid 5 as a yellow solid. The crude acid was recrystallized from hexane-ethanol to produce an analytically pure sample as bright yellow crystals: mp 164-7° C. $^1$H NMR ($CDCl_3$) δ 2.79 (s, 4H, $CH_2$), 2.08 (s, 6H), 1.42 (s, 12H). ESI MS (neg. ion mode) m/z 335 (M-H). UV $\lambda_{max}$ 257, 343 nm. Anal. Calcd for $C_{18}H_{24}O_6/NH_3$: C, 61.17; H, 7.70, N, 3.96, O, 27.16. The structure of the compound was confirmed by x-ray crystallography and shown in FIG. 4.

Example 3

Synthesis of Quinone Cross Linkers

A. Synthesis of Quinone Esters

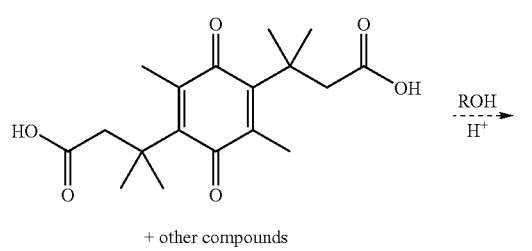

+ other compounds

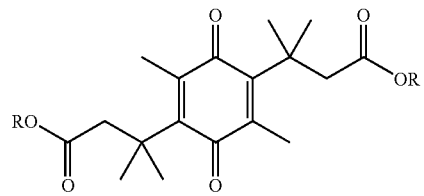

This example demonstrates an exemplary method of synthesizing a quinone ester. With time, the quinone acid can convert to a mixture of at least three compounds. This conversion is likely due to intramolecular Michael addition of the acid moiety to the quinone or to the carbonyl, much like what was observed by Cohen in a related compound (R. T. Borchardt and L. A. Cohen *J. Am. Chem. Soc.* 1973, 95, 8308). By analogy to Cohen's work, the product mixture will equilibrate and the equilibrating mixture can be converted into any desired ester, simply by stirring with the corresponding alcohol in the presence of an acid catalyst. Thus, any of the quinone esters for use as degradable cross-linking agents according to the methods of the present invention can be available by this or a related synthesis.

For example, the quinone acid chloride (product structure; R=Cl) can be generated by treatment of the equilibrating mixture with oxalyl chloride. The acid chloride can easily be converted into needed amides by treatment with the corresponding amines. Alternatively, amides can be prepared by reaction of the equilibrating mixture with the corresponding amines in the presence of N,N'-dicyclohexyl-carbodiimide (DCC) or other condensing agents, such as diisoproplycarbodiimide (DIC). In the DCC coupling method, the carboxylic acid initially will form a reactive intermediate with the carbodiimide, an O-acylisourea (Sheehan et al., *J. Am. Chem. Soc.,* 1955, 77, 1067-1068). Depending on the exact reaction conditions, the adduct can be converted into a symmetrical anhydride, in the presence of excess carboxylic acid, or into an active ester in the presence of a hydroxy component. In either case, insoluble dicyclohexylurea (DCU) is formed as co-product and the anhydride or active ester can be isolated.

The diisopropyl analog of DCC, N,N'-diisopropylcarbodiimide (DIC) is preferable in some embodiments since the corresponding urea derivative is more soluble in organic solvents such as DCM and DMF. For carbodiimide-mediated couplings, 1-hydroxybenzotriazole (HOBt) (König, W. and Geiger, R. *Chem. Ber.* 1970, 103, 2034-2040) can be added, generating an O-acyl-1-hydroxybenzotriazole, which is a very powerful acylating reagent. Alternatively, 3-hydroxy-4-oxo-3,4-dihydro-1,2,3-benzotriazine (Dhbt-OH) can be used.

In addition to DCC and DIC, several other in situ acylating reagents can be used, including, but not limited to, 2-(1H-benzotriazol-1-yl)-N,N,N',N'-tetramethyluronium hexafluorofluorophosphate (HBTU), 2-(1H-benzotriazol-1-yl)-N,N,N',N'-tetramethyluronium tetrafluoroborate, TBTU, (Dourtoglou, V. and Gross, B. *Synthesis* 1984, 573-574); BOP (benzotriazolyl N-oxytrisdimethaminophosphonium hexafluorofluorophosphate), and PyBOP (benzotriazolyl N-oxytrispyrrolidinophosphonium hexafluorofluorophosphate) (Coste, J. et al. *Tetrahedron Lett.* 1990, 31, 205-208), which all requiring the presence of an activating base.

B. Synthesis of Sulfones

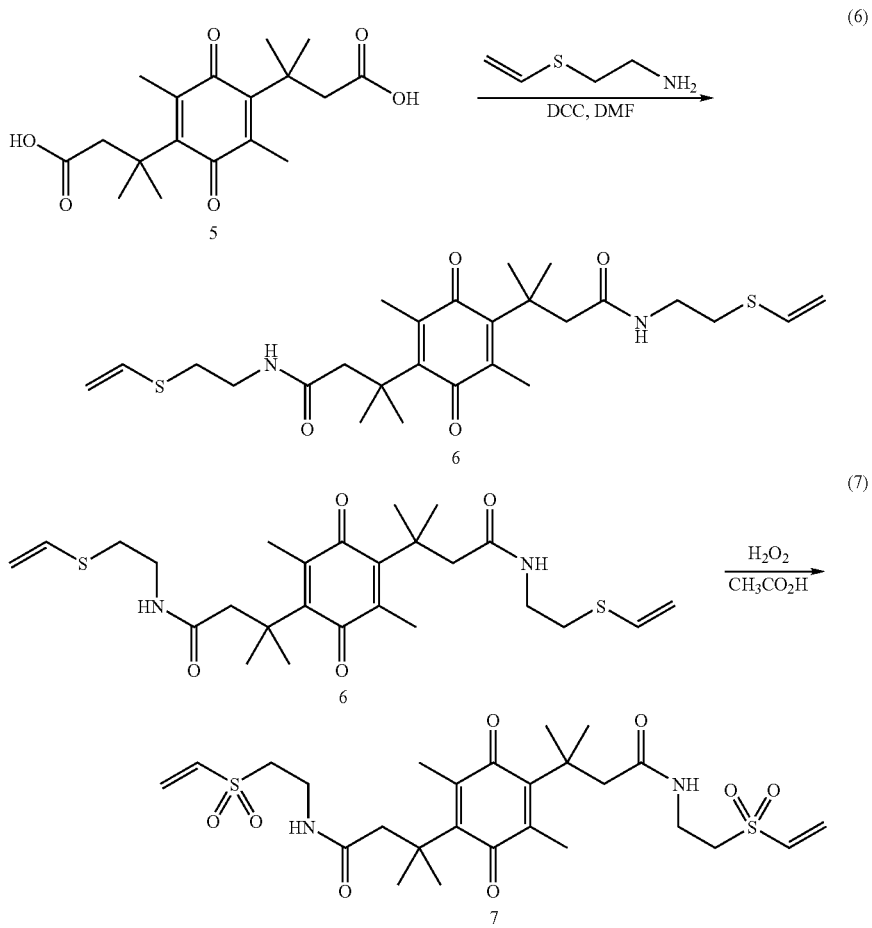

This example demonstrates an exemplary method of synthesizing a sulfone cross-linker. The quinone acid 5 (100 mg) was dissolved in a solution of the amine (67 mg, 2.2 eq) in dry DMF (5.0 mL) and DCC (135 mg, 2.2 eq) was added. The reaction was stirred at room temperature for 6 h, then evaporated to dryness. The residue was purified by chromatography (EtOAc-hexane, 1:5) providing the sulfide amide 6.

The sulfide amide 6 (10 mg) was added to a solution of 30% aqueous hydrogen peroxide (0.5 mL) in acetic acid (1.0 mL) at 0° C. The reaction mixture was stirred at 0° C. for 12 h, then allowed to warm to room temperature. The mixture was evaporated to dryness and then dissolved in EtOH. The ethanol solution of the sulfone 7 could be used directly in polymer cross-linking reactions. Preferably, the sulfone 7 should be prepared immediately prior to use.

While the present invention has been described in terms of specific methods and compositions, it is understood that variations and modifications will occur to those skilled in the art upon consideration of the present invention.

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

The invention claimed is:

1. An electrically-degradable polymer comprising:
polymer moieties comprising monomeric units, and
a quinone moiety, which is a crosslinking agent between non-terminal monomeric units in the polymer moieties, and the quinone moiety has the formula:

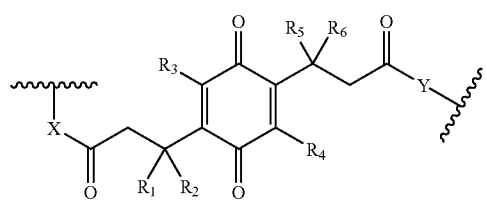

wherein
$R_1$, $R_2$, $R_5$, and $R_6$ are selected from alkyl, aryl, alcohol, ether, thiol, thioether, amine, cyano, halo, nitro, ketone, aldehyde, ester, amide, thioester, carbonate, carbamate, and urea,
$R_3$ and $R_4$ are selected from hydrogen, alkyl, aryl, alcohol, ether, thiol, thioether, amine, cyano, halo, nitro, ketone, aldehyde, ester, amide, thioester, carbonate, carbamate, and urea,
X and Y is each attached to a polymer moiety and can be the same or different and are selected from vinyl sulfone, epoxide, alkyl halide, alkene, amine, alcohol, acid halide, acid anhydride, sulfate, phosphate, isocyanate, isothiocyanate, and thiol alkyl groups, wherein X and Y are released from the quinone moiety upon reduction of the quinone, such that the polymer moieties are capable of degrading from the quinone moiety the upon exposure to a change in electric potential.

2. The electrically-degradable polymer moiety of claim 1, wherein the polymer further comprises monomers selected from styrene, acrylates, methacrylates, 1,3-butadiene, isoprene, 2-vinylpyridine, ethylene oxide, acrylonitrile, methyl vinyl ketone, alpha-cyanoacrylate vinylidene cyanide, propylene, butene, isobutylene, phosphorus acid, phosphonous acid, phosphinous acid, phosphoric acid, phosphonic acid, phosphinic acid, methylene bis(phosphonic acid), poly(vinylphosphonic acid), aziridine, spermine, cadaverine, and putrescine.

3. The electrically-degradable polymer moiety of claim 1, wherein the polymer is capable of degrading upon exposure to a change in electric potential of at least 0.05 V.

* * * * *